(12) United States Patent
Melief et al.

(10) Patent No.: US 7,563,445 B2
(45) Date of Patent: Jul. 21, 2009

(54) CD40 BINDING MOLECULES AND CTL PEPTIDES FOR TREATING TUMORS

(75) Inventors: Cornelis J. M. Melief, Haarlem (NL); Stephen P. Schoenberger, Encinitas, CA (US); Rienk Offringa, Leiden (NL); Rene Toes, Leiden (NL)

(73) Assignee: Keygene N.V., Wageningen (NL)

( * ) Notice: Subject to any disclaimer, the term of this patent is extended or adjusted under 35 U.S.C. 154(b) by 360 days.

(21) Appl. No.: 10/227,789

(22) Filed: Aug. 26, 2002

(65) Prior Publication Data

US 2003/0022860 A1    Jan. 30, 2003

Related U.S. Application Data

(63) Continuation of application No. 09/316,935, filed on May 22, 1999, now abandoned.

(60) Provisional application No. 60/086,625, filed on May 23, 1998.

(51) Int. Cl.
*A61K 39/395* (2006.01)
*A61K 39/12* (2006.01)
*A61K 38/08* (2006.01)

(52) U.S. Cl. .............. 424/173.1; 424/141.1; 424/153.1; 424/130.1; 424/184.1; 424/186.1

(58) Field of Classification Search .............. 424/173.1, 424/130.1, 184.1, 186.1, 141.1, 153.1
See application file for complete search history.

(56) References Cited

U.S. PATENT DOCUMENTS 5,874,082 A    2/1999    De Boer

FOREIGN PATENT DOCUMENTS

WO    WO 96/26735    *    9/1996
WO    97/41440 A1    11/1997

OTHER PUBLICATIONS

Yasutomi et al. (1995) J. Virol., vol. 69 (4), 2279-2284.*
Restifo et al (1993) J. Immunother., vol. 14, 182-190.*
Erdile et al. (2000) Cancer Immunology Immunotherapy 49 (8): 410-416.*
den Boer et al. (2001) J. Immunol., vol. 167, 2522-2528.*
Daisuke et al. (2000) Immunobiology, vol. 201 (5), 527-540.*
Barber et al. (1994) J. Exp. Med. vol. 180(4) 1191-1194.*
Novellino et al. (2005) Cancer Immunol. Immunother., vol. 54, 187-207.*
Feltkamp et al. (1993) Eur. J. Immunol., vol. 23, 2242-2249.*
Lipford, G. B., et al.; "Peptide Engineering Allows Cytotoxic T-Cell Vaccination Against Human Papiloma Virus Tumour Antigen, E6", *Immunology* 84:298-303 (1995).
Christ, M., et al., "Gene Therapy With Recombinant Adenovirus Vectors: Evaluation of the Host Immune Response", *Immunology Letters*, 57:19-25 (1997).
Naviaux, R. et al.; "Retroviral Vectors For Persistent Expression In Vivo", *Current Opinion in Biotechnology* 3:540-547 (1992).
Gunzberg, W. H. et al.; "Virus Vector Design In Gene Therapy", *Molecular medicine today*, vol. 1(9), pp. 410-417 (1995).
Urvanelli, D., et al., "C-Terminal Domain Of The Adenovirus E1A Oncogene Product Is Required For Induction of Cytotoxic T Lymphocytes And Tumor-Specific Transplantation Immunity", Virology 173:607-614 (1989).
Funakoshi, D., et al.; Inhibition Of Human B-Cell Lymphoma Growth By CD40 Stimulation, *Blood*, vol. 83(10), pp. 2797-2794 (1994).
Tong, Alex. W. Et Al; "Anti-CD40 Antibody Binding Modulates Human Multiple Myeloma Clonogenicity In Vitro", Blood, vol. 84(9), pp. 3026-3033 (1994).
Mendoza et al., Cutting Edge: Immunostimulatory Effects of a Plasmid Expressing CD40 Ligand (CD154) on Gene Immunization, The Journal of Immunology 1997, pp. 5777-5781.

* cited by examiner

*Primary Examiner*—Anne Marie S Wehbe
(74) *Attorney, Agent, or Firm*—Browdy and Neimark, P.L.L.C.

(57) ABSTRACT

Disclosed is a method and composition for treating tumors or infectious diseases, wherein the composition includes CD40 binding molecules together with CTL-activating peptides, e.g., tumor antigens. Such composition is useful for enhancing the anti-tumor effect of a peptide tumor vaccine, or for otherwise activating CTLs so that the activated CTLs can act against tumorous or infected cells. The CD40 binding molecules can include antibody molecules, as well as homologues, analogues and modified or derived forms thereof, including immunoglobulin fragments like Fab, $(Fab')_2$ and Fv, as well as other molecules including peptides, oligonucleotides, peptidomimetics and organic compounds which bind to CD40 and activate the CTL response.

15 Claims, 9 Drawing Sheets

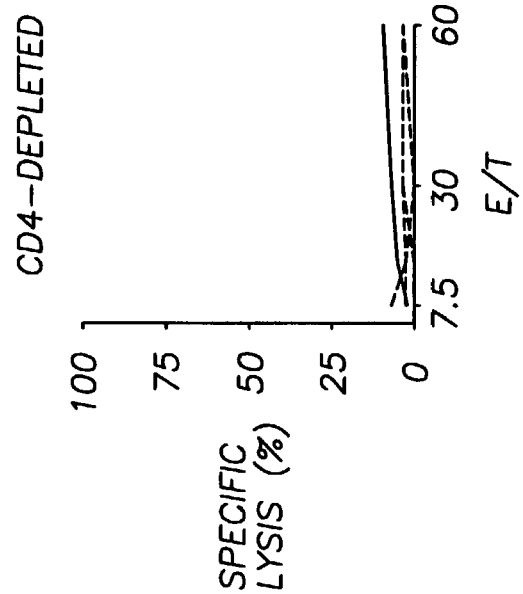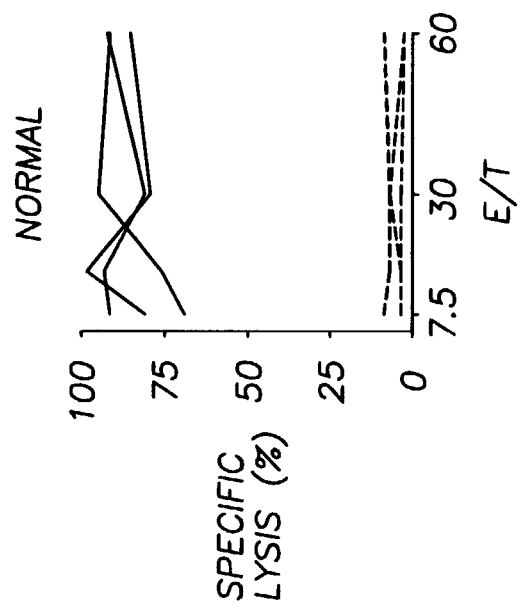

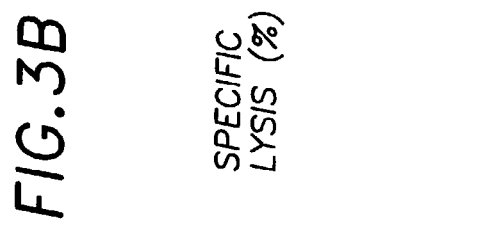
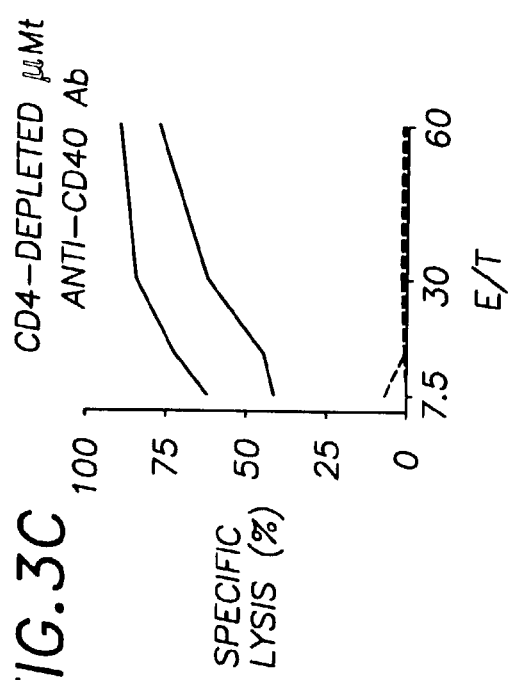
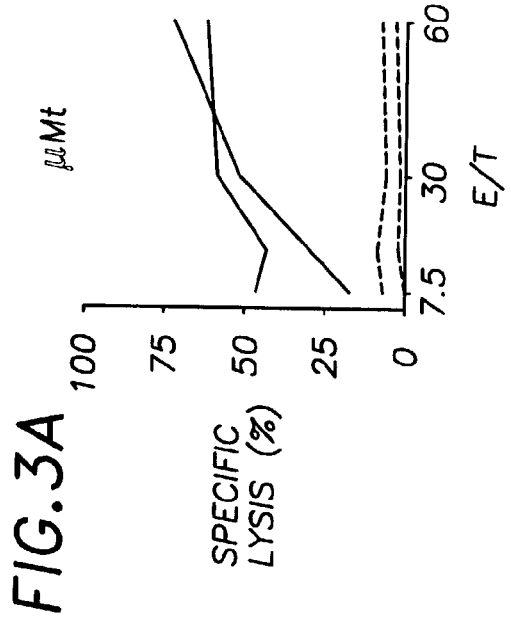

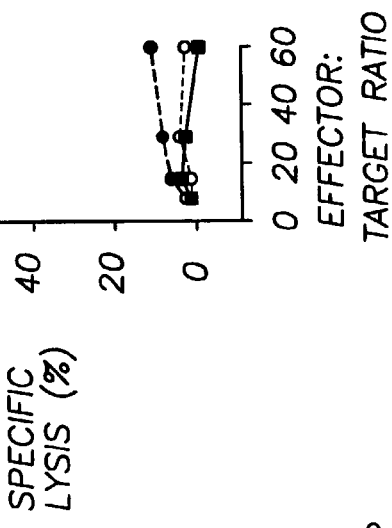
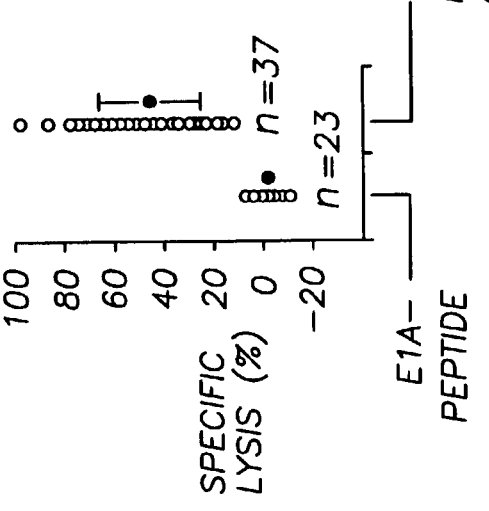
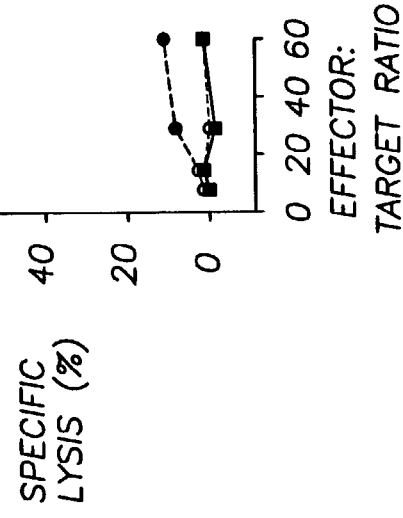

CD40 BINDING MOLECULES AND CTL PEPTIDES FOR TREATING TUMORS

CROSS REFERENCE TO RELATED APPLICATIONS

The present application is a continuation of and claims priority to U.S. patent application Ser. No. 09/316,935, filed May 22, 1999 now abandoned, which claims priority to U.S. Provisional Application No. 60/086,625, filed May 23, 1998, both of which are incorporated herein by reference.

FIELD OF THE INVENTION

The invention includes CD40 binding molecules together with CTL-activating peptides, including tumor antigens, in a pharmaceutical composition.

BACKGROUND OF THE INVENTION

Many tumors escape surveillance by our immune system. In cancer patients there is clearly a quantitative and/or qualitative defect in the immune system's specific mechanisms to delete tumor cells. One of these mechanisms is provided by the cytotoxic T cells (CTL) that can recognise and kill cells infected by virus or transformed into cancer cells. Previously it was postulated that dendritic cells (DC) stimulate T-helper cells which, in turn, provide help for the activation of CTL. The present inventors have demonstrated that the T-helper cell is not providing helper signals directly to the CTL (by secretion of IL2), but rather, the T-helper cell is providing a signal to the DC that induces yet uncharacterised cell surface and/or soluble molecules that can activate CTL in the absence of T-helper cells. The signal provided by the T-helper cell to the DC is mediated by CD40L-CD40 interaction. This novel finding has provided an unique opportunity for cancer immunotherapy.

The immune system is capable of killing autologous cells when they become infected by virus or when they transform into cancer cells. Such a potentially dangerous mechanism must, clearly, be under tight control. The immune system's CTL circulate as inactive precursors. To be activated, the precursor T-killer cell must recognise its specific antigen peptide, which is presented as MHC class I molecules on professional APC. However, in order to prime these T cells, the APC also need to present the antigen in a proper costimulatory context as provided by, amongst others, the costimulatory surface molecules B7.1 and B7.2 and by the lympokine IL-12.

Until recently it was believed that a T-helper cell that recognises the same antigen on the same APC is needed to fully activate the CTL. The specific T-helper cell would supply cytokines such as IL-2 needed for the activation of the CTL. Guerder and Matzinger (*J. Exp. Med.* 176:553 (1992)), however, proposed the "licensing" model for CTL activation. In this model it was suggested that the T-helper cell, when recognising its antigen on a professional APC, would deliver an activation signal to the APC that as a result would be able to subsequently activate a CTL without the need for the T-helper cell to be present. Only very recently, the molecular mechanism of the licensing model has been elucidated. Schoenberger et al. (*Nature* 393:480 (1998)), described the role of the CD40L-CD40 pathway in the licensing model. Interaction between T-helper cell and DC through the CD40-CD40L binding results in activation of the DC, thereby enabling the DC to efficiently prime naive CTL.

DC circulate through the tissues of our body and in this manner can collect, process and present antigens. After collection of antigens, they migrate to the draining lymph nodes where they present antigen to the T cells. It is well known that a DC needs to be activated to perform optimally. Resting DC express only modest levels of MHC and costimulatory molecules and are poor stimulators of T cells. DC can be activated by inflammatory cytokines and bacterial products, which results in upregulation of MHC and costimulatory molecules. Activation of DC into fully mature DC, expressing optimal levels of MHC molecules, costimulatory molecules and lymphokines such as IL-12, requires additional triggering of these cells through the CD40 receptor. Consequently, the combination of inflammatory cytokines at the site of antigen uptake and the CD40L-CD40 interaction during the T-helper cell interaction result in an optimal capacity to license the DC for CTL activation.

Many tumors escape immune surveillance by specific CTL mechanisms. If DC gather tumor antigens under non-inflammatory conditions the number of T-helper cells that are activated may be to low to induce enough CTL to be activated to induce an appropriate anti-tumor response. This concept has prompted investigators to help the immune system by administration of cytokines such as IL-2 and IL-12 that directly stimulate CTL activity or by boosting antigen presentation by administration of tumor cells transfected with GM-CSF. These strategies have met variable but encouraging results.

It is clear that there is still a great need to find ways to generate and/or enhance protective anti-tumor responses involving cellular and humoral immunity. The CD40 activation pathway was found to be a major immunoregulatory pathway for the generation of primary humoral and cellular immune responses. As described above, the CD40 pathway on DC is responsible for the induction of anti-tumor CTL responses. In addition, activation of the CD40 pathway on macrophages stimulates a strong tumoricidal activity.

SUMMARY OF THE INVENTION

The invention includes CD40 binding molecules together with CTL-activating peptides, including tumor antigens in a pharmaceutical composition. Such composition is useful for enhancing the anti-tumor effect of a peptide tumor vaccine, or for otherwise activating CTLs so that the activated CTLs can act against tumorous or infected cells. The CD40 binding molecules can include antibody molecules, as well as homologues, analogues and modified or derived forms thereof, including immunoglobulin fragments like Fab, (Fab')$_2$ and Fv, as well as small molecules including peptides, oligonucleotides, peptidomimetics and organic compounds which bind to CD40 and activate the CTL response. CTL-activating peptides include the adenovirus-derived E1A peptide, having the sequence SGPSNTPPEI (SEQ ID NO:2), and the HPV16 E7 peptide derived from human papillomavirus type 16, having the sequence RAHYNIVTF (SEQ ID NO:3).

The CD40 binding molecule and the CTL activating peptide can be administered to a patient by suitable means, including injection, or gene constructs encoding such a molecule and a peptide can be administered, and the molecule and peptide thereby produced in vivo or ex vivo. Such a gene therapy is conducted according to methods well known in the art. If the transfection or infection of the gene constructs is done ex vivo, the infected or transfected cells can be administered to the patient, or these steps can be done in vivo whereby the molecule and the peptide are produced endogenously. The transfection or infection, if done ex vivo, can be by conventional methods, including electroporation, calcium phosphate transfection, micro-injection or by incorporating the gene constructs into suitable liposomes. Vectors, including a retrovirus, adenovirus or a parvovirus vector, or plasmids, can be used to incorporate the gene constructs, which are then expressed in vivo or ex vivo.

It is demonstrated herein that T-cell help for CTL priming is mediated through CD40-CD40Ligand (CD40L) interactions, and that lack of CTL priming in the absence of CD4+ T cells can be restored by monoclonal antibody (mAb)-mediated CD40 activation of bone marrow-derived APC in the presence of CTL-activating peptides including tumor antigens. Furthermore, blockade of CD40L, expressed by CD4+ T cells, results in the failure to raise CTL immunity. This defect can be overcome by in vivo CD40-triggering. In vivo triggering of CD40 can markedly enhance the efficacy of peptide-based anti-tumor vaccines, or otherwise activate CTLs to result in an anti-tumor or anti-infected cell reaction.

It is also noted that a CTL-activating peptide can become tolerogenic, meaning that the host reaction against cells expressing such peptide is inhibited, in the absence of anti-CD40. However, such a peptide combined with an activating anti-CD40 antibody converts tolerization into strong CTL activation. Moreover, as noted above, CD40-ligation can provide an already protective tumor-specific peptide-vaccine with the capacity to induce therapeutic CTL immunity in tumor-bearing mice.

These findings together demonstrate that the CD40-CD40Ligand pair acts as a switch determining whether naive peripheral CTL are primed or tolerized, Therefore CD40-binding agents such as monoclonal antibodies and other stimulatory ligands can be effectively used in combination with a CTL-activating peptide.

BRIEF DESCRIPTION OF THE FIGURES

FIG. 1: Cross-priming of E1B-specific CTLs requires CD4+ T helper cells

Figure 2B:
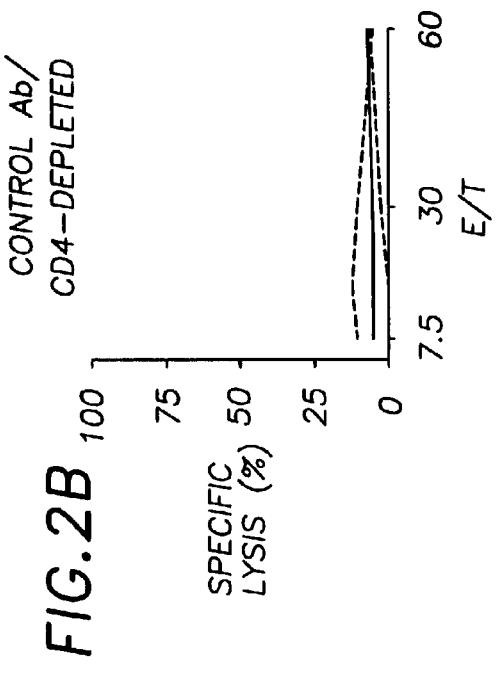

Splenocytes from normal (a) or CD4-depleted B6 (b) mice immunized with Ad5EI-BALB/c MECs were tested at various effector/target ratios for lysis of syngeneic MEC target cells loaded with the $E1B_{192-200}$ peptide (solid lines), which is derived from human adenovirus and has the sequence VNIRNCCYI (SEQ ID NO:1)or a $D^d$-restricted control peptide HPV-16 $E7_{49-57}$ (dashed lines). Each line represents one mouse. Data shown represent one experiment of three performed with similar results.

FIG. 2: CD40 activation replaces CD4+ T helper cells

Splenocytes from CD4-depleted (a, b) or classII-deficient I-Ab-knockout (KO) (c,d) B6 mice were immunized with Ad5E1-BALB/c MECs and treated with either the CD40-activating antibody (Ab) FGK45 (a, c) or an isotype control antibody (b, d). These splenocytes were tested for E1B-specific CTL activity on syngeneic MEC target cells loaded with either the $E1B_{192-200}$ peptide (solid lines) or the HPV-16 $E7_{49-57}$ control peptide (dashed lines). Each line represents a single mouse. Data depicted are from two independent experiments. E/T ratio, effector/target ratio.

FIG. 3: B cells are not essential as cross-priming APCs or for anti-CD40-mediated restoration of cross-priming Spenocytes were taken from untreated (a), CD4-depleted B-cell-deficient B6 MT mice (b, c), which were immunized with Ad5E1-BALB/c MECs and which received either an isotype control antibody (b) or the CD40-activating antibody FGK45 (c). These splenocytes were tested for E1B-specific CTL activity on syngeneic MEC target cells loaded with either the $E1B_{192-200}$ peptide (solid lines) or the HPV $E7_{49-57}$ control peptide (dashed lines). Each line represents one mouse. Data shown represent one experiment of two performed with similar results.

FIG. 4: CD40L blockade-prevents cross-priming of E1B-specific CTLs

Splenocytes were taken from B6 mice immunized with Ad5E1-BALB/c MECs and treated with the CD40L-blocking antibody MR-1 (a), or control antibody (b), or from mice treated with the CD40L-blocking antibody MR-1 in combination with the CD4 0-activating antibody FGK45 (c) 24 h after immunization. These splenocytes were tested for E1B-specific CTL activity on syngeneic MEC target cells loaded with the $E1B_{192-200}$ peptide (solid lines) or the HPV-16 $E7_{49-57}$ control peptide (dashed lines). Each line represents one mouse. Data shown represent one experiment of three performed with similar results. E/T ratio, effector/target ratio.

FIG. 5: Mice injected s.c. with the E1A-peptide are no longer able to mount E1A-specific CTL C57BL/6 mice were injected twice s.c. (1 week interval) with 20 μg E1A-peptide (a, b) or control-peptide (c, d) in IFA, and challenged i.p. 1 day later with SAMB7 (b, d), a cell line expressing high amounts of E1A-peptide. Bulk cultures derived from these mice were tested for E1A-specific cytotoxicity on target cells pulsed with the E1A-peptide (-■-) or the HPV16 E7-peptide (-○-). Specific lysis of representative bulk cultures at different effector to target (E/T) ratios is shown. This experiment has been repeated 4 times with comparable results.

Figure 6:
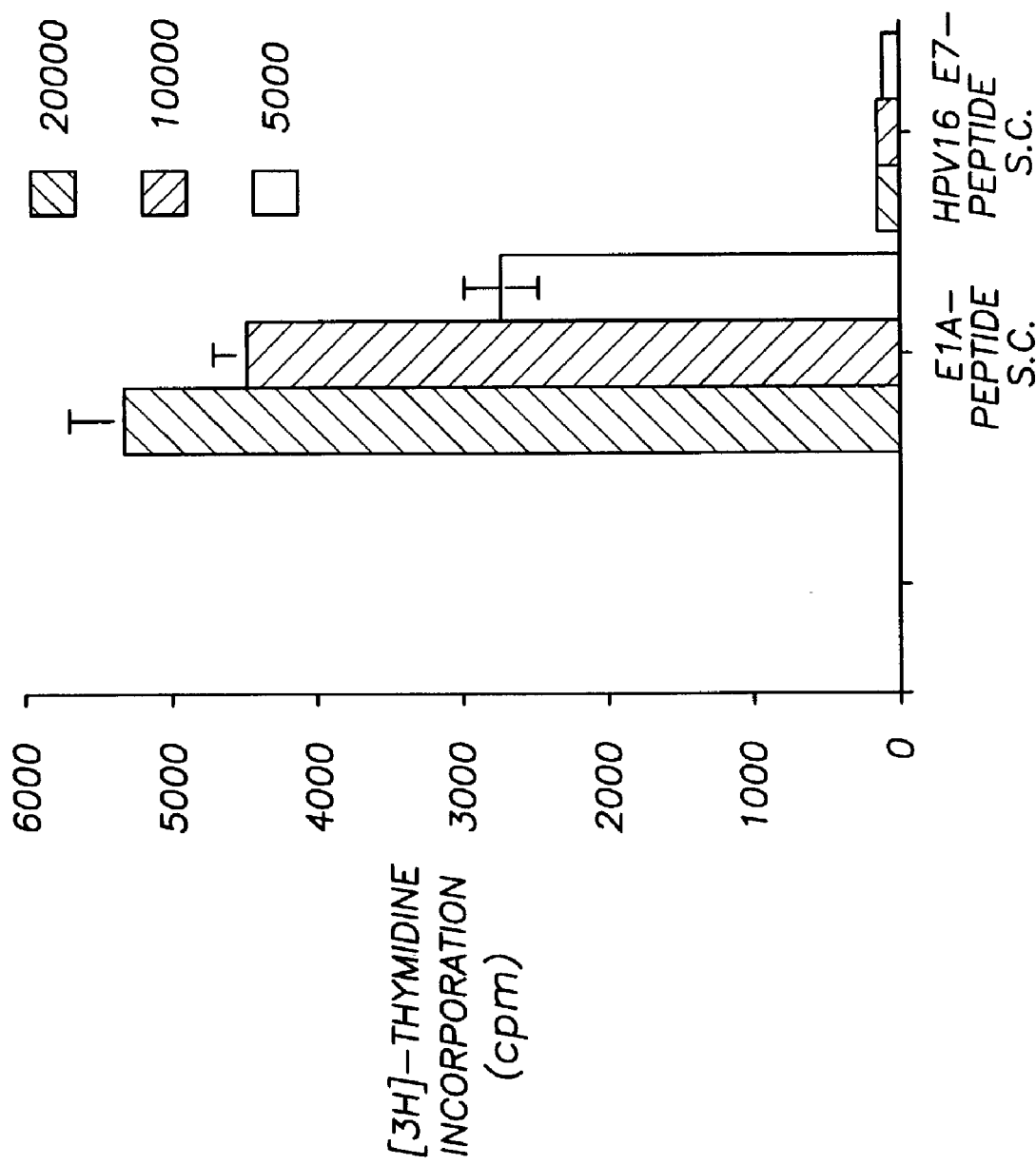

FIG. 6: Tolerizing E1A-peptide is rapidly distributed systemically after s.c. injection in IFA Spleen cells derived from untreated C57BL/6 mice (–), or from mice injected s.c. 16 h earlier with 100 μg of E1A- or HPV16 E7-peptide in IFA were used as stimulator cells for an E1A-specific CTL clone. [$^3$H]-thymidine incorporation (cpm) +/−S. E. M. is shown for different effector to stimulator concentrations,. without subtraction of background counts. Results are representative of 5 independent experiments.

Figure 7B:
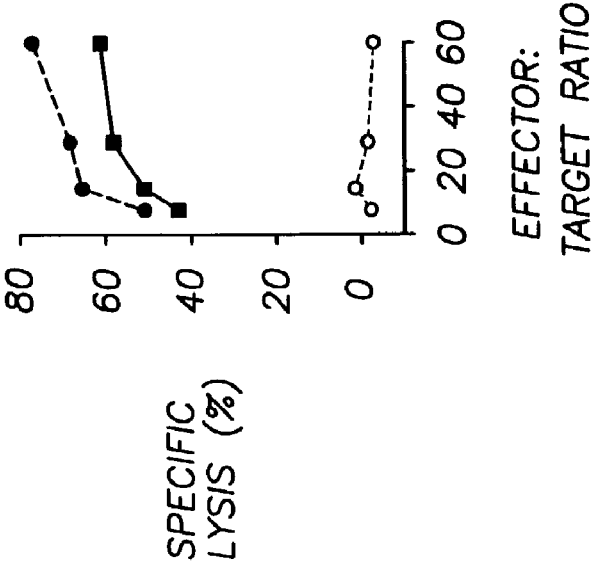
Figure 7A:
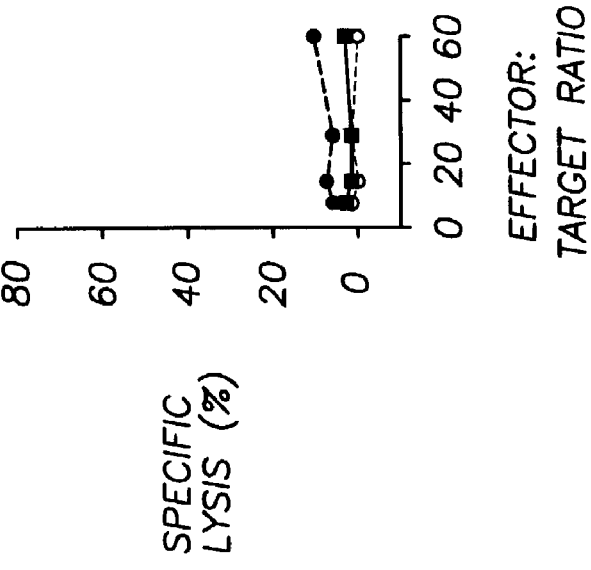

FIG. 7: CTL-tolerance induction is reverted into CTL-priming after CD40-triggering in vivo Wild type C57BL/6 mice (a, b) and H-$2^b$ CD40 $^{-/-}$ mice (c, d) were injected s.c. with 20 μg E1A-peptide in IFA alone (c), in combination with a rat IgG2a control antibody (a), or in combination with the anti-CD40 mAb FGK-45 (b, d). Bulk cultures from these mice were tested for E1A-specific cytotoxicity on target cells pulsed with the E1A-peptide (-■-), the HPV16 E7-peptide (-○-) or Ad5E1 transformed tumor cells (-♦-). Specific lysis of representative bulk cultures at different E/T ratios is shown. This experiment has been repeated 18 (B6 mice) and 2 (CD40−/− mice) times, respectively, with comparable results. In (e) the % specific lysis of 23 respectively 37 bulk CTL cultures derived from B6 mice injected with E1A-peptide in IFA alone (left) or in combination with the anti-CD40 mAb (right) at an E/T of 60 is shown. Mean plus standard deviation of each group are shown (E1A versus E1A+anti-CD40: p<0.01, student t-test).

Figure 8B:
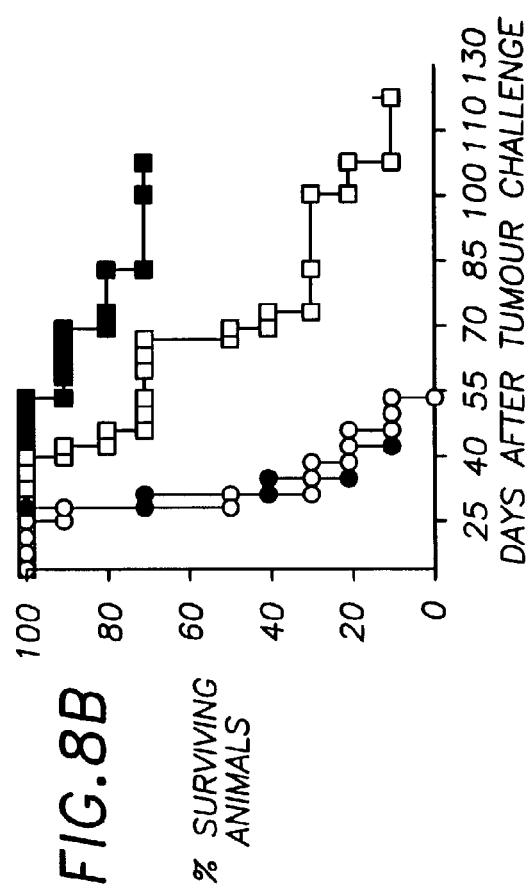
Figure 8A:
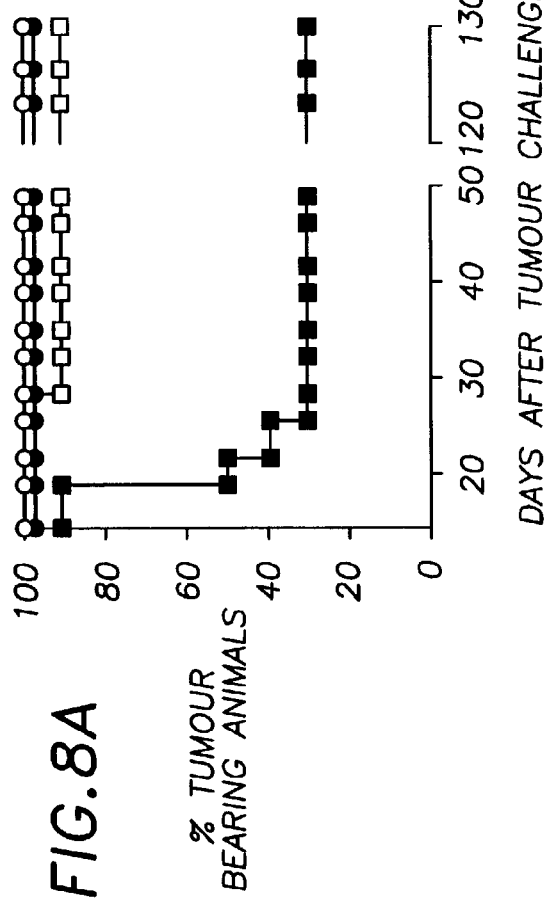

FIG. 8: Therapy of HPV16 E6 and E7 transformed cells by combination treatment of peptide together with in vivo CD40 triggering Mice were injected s.c with 25.000 HPV16 transformed syngeneic cells (TC-1). C57BL/6 mice were left untreated (-○-) or after 6 days received 100 μg HPV16 E7-peptide i.p. in IFA (-□-), 100 μg HPV16 E7-peptide i.p. in IFA in combination with the anti-CD40 mAb FGK-45 (-■-) or a control peptide i.p. in IFA in combination with the anti-CD40 mAb FGK-45 (-●-). The percentage of tumor bearing mice is depicted for different treatment groups (n=10) in (a). The differences between the group treated with the HPV16-peptide plus the anti-CD40 mAb and the other three groups were statistically significant (p<0.01) (Log-Rank test). In (b) the percentage of surviving animals is shown (E7-peptide-treated group vs E7-peptide plus anti-CD40-treated group: p=0.002, Log-Rank test).

MAKING AND USING THE INVENTION

The CD40 binding molecules of the invention can be made by conventional production and screening techniques. A rat and a hamster anti-mouse CD40 monoclonal antibody ("Mabs") are each described in Nature 393: 474-77 (1998) and are available commercially (Pharmingen, Inc., Calif.). The anti-mouse CD40 MAb, designated FGK45, which is used in the experiments described below, is described by Rolink. A. et al., Immunity 5, 319-330 (1996). Anti-human CD40 MAbs can be made following techniques well-known in the art, and described by G. Kohler and C. Milstein (Nature, 1975: 256: 495-497). MAbs can be raised by immunizing rodents (e.g. mice, rats, hamsters and guinea pigs) with either native CD40 as expressed on cells or purified from human plasma or urine, or recombinant CD40 or its fragments, expressed in a eukaryotic or prokaryotic system. Other animals can be used for immunization, e.g. non-human primates, transgenic mice expressing human immunoglobulins and severe combined immunodeficient (SCID) mice transplanted with human B lymphocytes. Hybridomas can be generated by conventional procedures by fusing B lymphocytes from the immunized animals with myeloma cells (e.g. Sp2/0 and NSO), as described by G. Köhler and C. Milstein Id. In addition, anti-CD40 MAbs can be generated by screening of recombinant single-chain Fv or Fab libraries from human B lymphocytes in phage-display systems. The specificity of the MAbs to CD40 can be tested by enzyme linked immunosorbent assay (ELISA), Western immunoblotting, or other immunochemical techniques. The activating activity of the antibodies on CTLs, in combination with a CTL-activating peptide, can be assessed using the assays described in the Examples below.

For treating humans, the anti-CD40 MAbs would preferably be used as chimeric, Deimmunised, humanized or human antibodies. Such antibodies can reduce immunogenicity and thus avoid human anti-mouse antibody (HAMA) response. It is preferable that the antibody be IgG4, IgG2, or other genetically mutated IgG or IgM which does not augment antibody-dependent cellular cytotoxicity (S.M. Canfield and S. L. Morrison, J. Exp. Med., 1991: 173: 1483-1491) and complement mediated cytolysis (Y. Xu et al., J Biol. Chem., 1994: 269: 3468-3474; V.L. Pulito et al., J Immunol., 1996; 156: 2840-2850).

Chimeric antibodies are produced by recombinant processes well known in the art, and have an animal variable region and a human constant region. Humanized antibodies have a greater degree of human peptide sequences than do chimeric antibodies. In a humanized antibody, only the complementarity determining regions (CDRs) which are responsible for antigen binding and specificity are animal derived and have an amino acid sequence corresponding to the animal antibody, and substantially all of the remaining portions of the molecule (except, in some cases, small portions of the framework regions within the variable region) are human derived and correspond in amino acid sequence to a human antibody. See L. Riechmann et al., Nature, 1988; 332: 323-327; G. Winter, U.S. Pat. No. 5,225,539; C.Queen et al., U.S. Pat. No. 5,530,101.

Deimmunised antibodies are antibodies in which the T and B cell epitopes have been eliminated, as described in in International Patent Application PCT/GB98/01473. They have reduced immunogenicity when applied in vivo.

Human antibodies can be made by several different ways, including by use of human immunoglobulin expression libraries (Stratagene Corp., La Jolla, Calif.) to produce fragments of human antibodies (VH, VL, Fv, Fd, Fab, or (Fab')$_2$, and using these fragments to construct whole human antibodies using techniques similar to those for producing chimeric antibodies. Human antibodies can also be produced in transgenic mice with a human immunoglobulin genome. Such mice are available from Abgenix, Inc., Fremont, California, and Medarex, Inc., Annandale, New Jersey.

One can also create single peptide chain binding molecules in which the heavy and light chain Fv regions are connected. Single chain antibodies ("ScFv") and the method of their construction are described in U.S. Pat. No. 4,946,778. Alternatively, Fab can be constructed and expressed by similar means (M. J. Evans et al., J Immunol. Meth., 1995; 184: 123-138). All of the wholly and partially human antibodies are less immunogenic than wholly murine MAbs, and the fragments and single chain antibodies are also less immunogenic. All these types of antibodies are therefore less likely to evoke an immune or allergic response. Consequently, they are better suited for in vivo administration in humans than wholly animal antibodies, especially when repeated or long-term administration is necessary. In addition, the smaller size of the antibody fragment may help improve tissue bioavailability, which may be critical for better dose accumulation in acute disease indications, such as tumor treatment.

Based on the molecular structures of the variable regions of the anti-CD40 mAbs or the known CTL-activating peptides, one could use molecular modeling and rational molecular design to generate and screen molecules which mimic the molecular structures of the binding region of the antibodies or the peptides, respectively, and activate CTLs. These small molecules can be peptides, peptidomimetics, oligonucleotides, or other organic compounds. The mimicking molecules can be used for treatment of cancers and infections. Alternatively, one could use large-scale screening procedures commonly used in the field to isolate suitable molecules from libraries of compounds.

The dosage for the molecules of the invention can be readily determined by extrapolation from the in vitro tests and assays described below, or from animal experiments or from human clinical trials. The molecules of the invention would be preferentially administered by injection, in the case of antibodies or proteins, although certain small molecules may be suited for oral administration. The assays and tests demonstrating the efficacy of the invention are described below.

EXAMPLE 1

Signaling Through CD40 can Replace CD4+ Helper T Cells in CTL, Priming

A well characterized model system to probe the mechanism of T-cell help for the, primary activation of CD8+ CTL responses in vivo was used. C57BL/6 (with the major histocompatibility complex (MHC) H-2$^b$) mice immunized with allogenic BALB/c (H-2$^d$) mouse embryo cells (MECs) expressing the human adenovirus type 5 early region 1 (Ad5EI-BALB/c MECs) generated strong CTL responses against an H-2D$^b$-restricted epitope of the adenovirus EIB protein (EIB$_{192-200}$) (FIG. 1a). As the allogeneic H-2$^d$ MHC molecules expressed by the Ad5EI-BALC/c MECs cannot prime H-2$^b$-restricted host CTLs, generation of E1B-specific CTLs must require cross-priming, that is, the uptake and H-2$^b$-restricted re-presentation of antigen by host APCs. Cross-priming of EIB-specific CTLs is strictly helper-dependent (FIG. 1b), as mice depleted of CD4$^+$ T-helper (T$_h$) cells before immunization no longer mounted an E1B-specific CTL response.

Figure 2D:
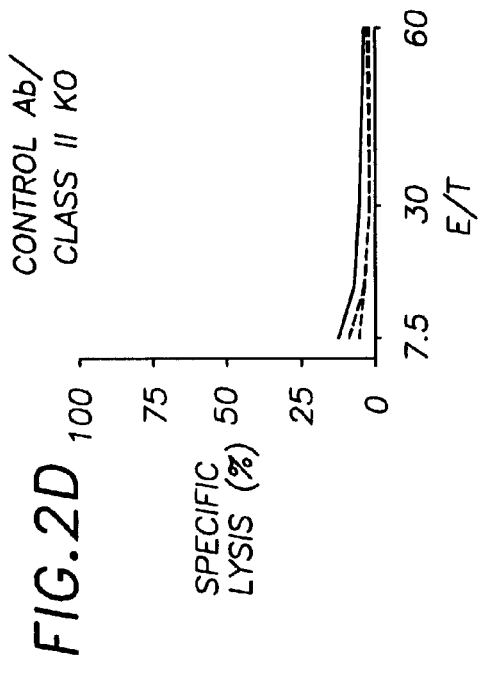
Figure 2A:
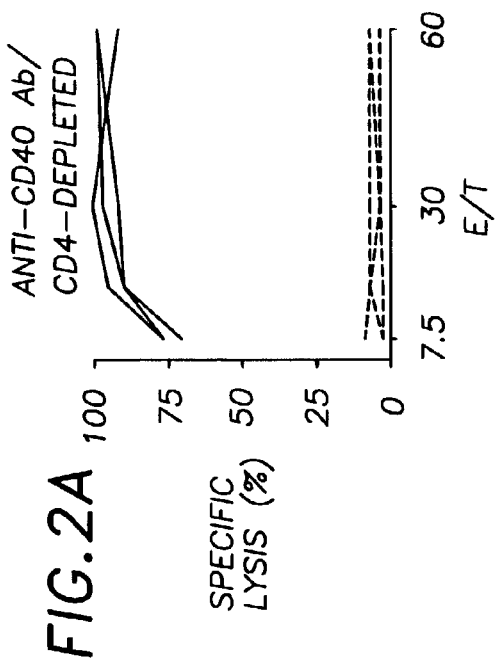
Figure 2C:
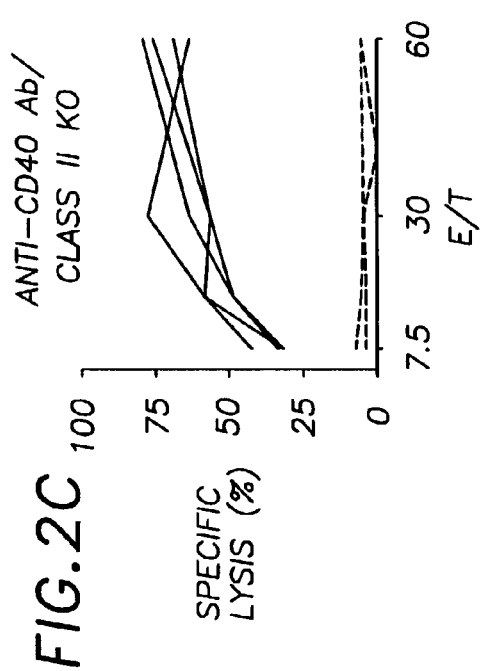

To investigate whether signalling through CD40 can replace CD4$^+$ helper T cells in CTL priming, mice were depleted of CD4$^+$ T cells in vivo before immunization with Ad5E1BALB/c MECs. One day after immunization, the mice received a single injection of the activating antibody antimouse CD40 mAb FGK45, or of an isotype-matched control antibody. Administration of FGK45 to CD4-depleted, immunized mice resulted in the efficient restoration of E1B-specific CTL responses (FIG. 2a) whereas treatment with the control antibody did not (FIG. 2b). Priming of E1B-specific CTLs was not detected in naive mice treated with FGK45 alone (not shown). To address the possibility that the effect of FGK45 was mediated through remaining D4$^+$ cells that were not depleted by treatment with the anti-CD4 antibody, B6 I-A$^b$ knockout mice, which lack mature functional CD4$^+$ peripheral T cells, were immunized with the Ad5EI-BALB/c MECs. The response to immunization in these mice mirrors that seen in the CD4-depleted mice, in that E1B-specific CTLs were detectable only in mice receiving the CD40-activating antibody (FIG. 2c), and not in those receiving the control antibody (FIG. 2d).

It was also studied whether the requirement for anti-CD40 antibodies in priming of CTLs in CD4-depleted mice could be replaced by bacterial lipopolysaccharide (LPS) (50 µg intravenous), a potent inducer of proinflammatory cytokines, or by administration of IL-2 (1×10$^5$ units in incomplete Freund adjuvant, subcutaneous) following immunization with Ad5EI-BALB/c MECs. Whereas CD4-depleted mice treated with FGK45 exhibited strong E1B-specific CTL activity, neither LPS or IL-2 treatment resulted in detectable CTL priming (not shown).

Ligation of CD40 on B cells upregulates their costimulatory activity, suggesting a role for these cells in the restoration of CTL priming by treatment with CD40 activating antibodies. To address this question, B6 MT mice, which lack mature B cells, were immunized with the allogeneic Ad5EI-BALB/c MECs. Cross-priming of E1B-specific CTLs did not require mature B cells (FIG. 3a). However, when depleted of CD4$^+$ cells, the B-cell deficient mice did not generate an E1B-specific CTL response (FIG. 3b). Activation through CD40 with the FGK45 monoclonal antibody completely restored the capacity of CD4-depleted MT mice to prime E1B-specific CTLs (FIG. 3c). Thus B cells are not required as APCs or accessory cells for cross-priming in this model system, nor are they required for CD40-mediated restoration of cross priming of CTLs in the absence of CD4$^+$ helper T cells. These results demonstrate that activation of bone marrow derived APC through CD40 can bypass the requirement for CD4$^+$ T-helper cells in the cross-priming of E1B-specific CTLs.

EXAMPLE 2

Figure 4B:
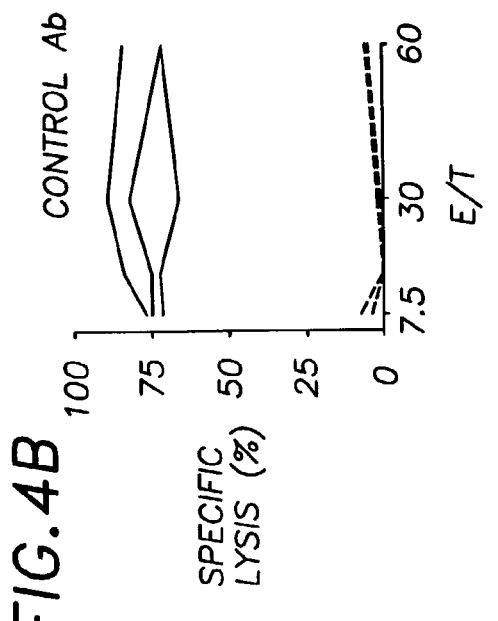
Figure 4A:
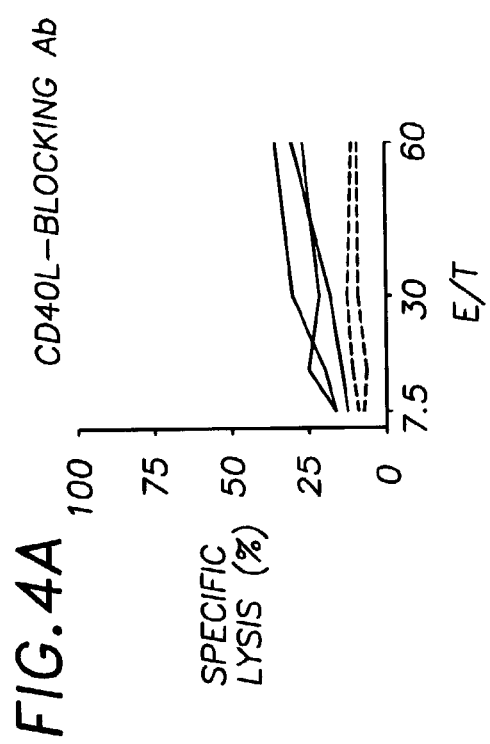
Figure 4C:
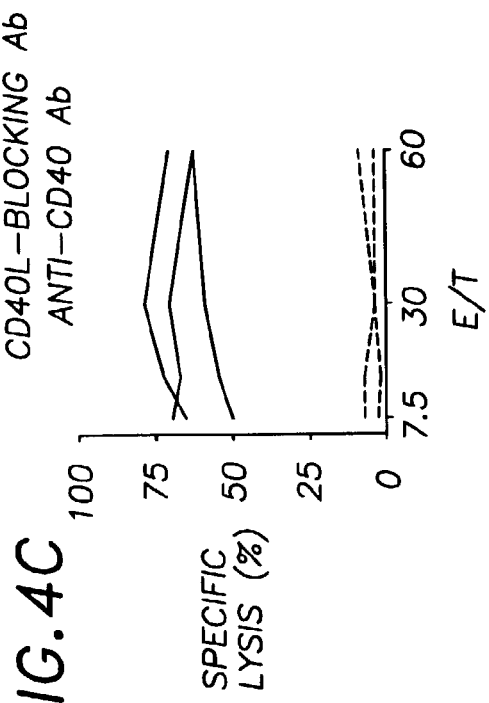

Blocking the Ability of CD4$^+$ Helper T Cells to Interact with APC Through the CD40L-CD40 Pathway Prevents Antigen-specific CTL Responses in Normal Mice If the CD40L-CD40 interaction represents the physiological pathway used by CD4$^+$ helper T cells to help CTLs, blocking the ability of the CD4$^+$ T cells to interact with APC through CD40L-CD40 interaction would be expected to diminish priming of E1B-specific CTL responses in normal mice. B6 mice were immunized with Ad5E1-BALB/c MECs and then treated with either the CD40L-blocking antibody MR1, or control antibody. Blockade of CD40L results in drastically reduced E1B-specific CTL responses (FIG. 4a) compared to the efficient CTL priming seen in mice receiving the control antibodies (FIG. 4b). The priming defect induced by CD40L blockade was fully restored following CD40 signalling by FGK45 (FIG. 4c). Thus the defect in CTL-priming induced by CD40L blockade lies in the failure of TH cells to transmit, rather than to receive, CD40L-mediated signals.

EXAMPLE 3

E1A-specific CTL Unresponsiveness After Peptide Administration

Figure 5A:
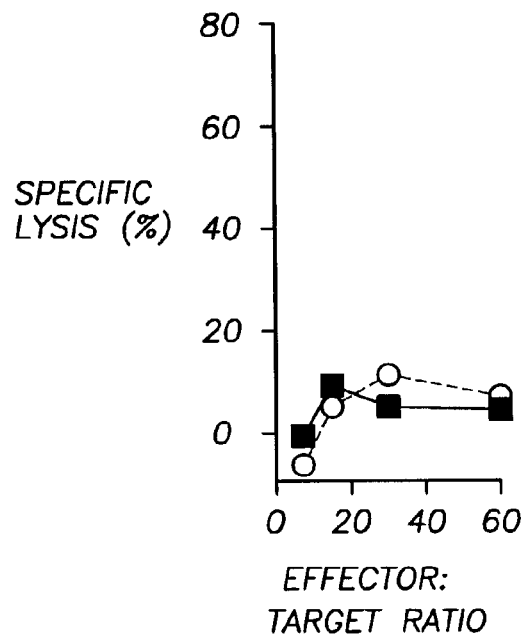
Figure 5B:
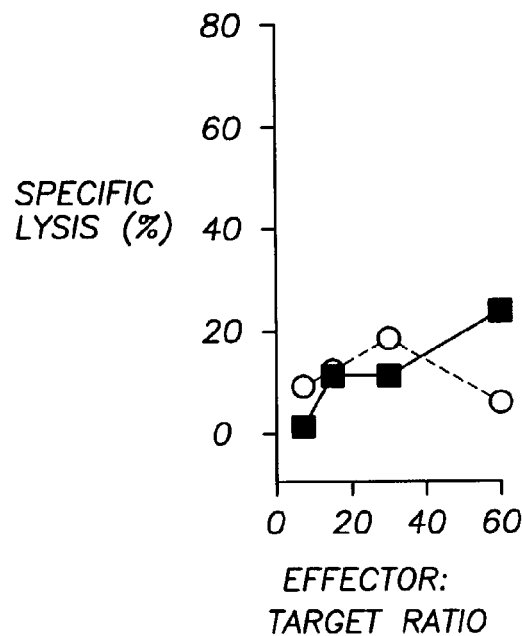
Figure 5C:
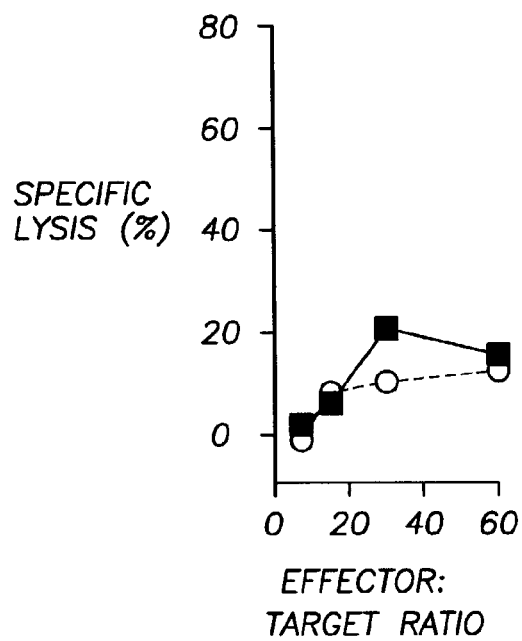
Figure 5D:
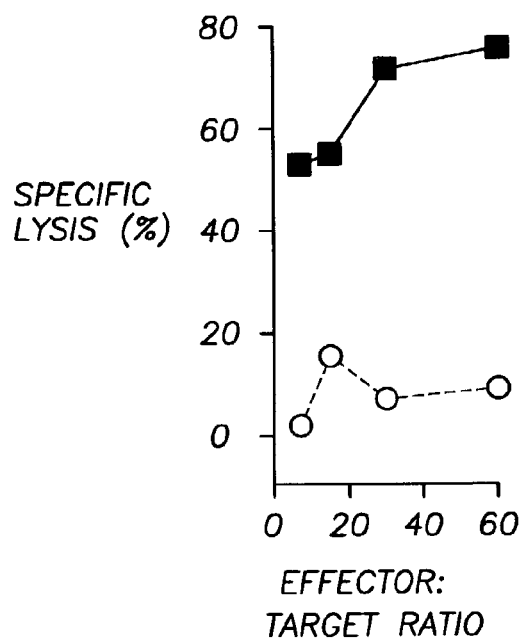

A previously described model system has been used (Toes et al., J. Immunol. 156:3911 (1996)). It has been shown that s.c. vaccination with the Ad5E1A-derived CTL epitope SGPSNTPPEI (SEQ ID NO: 2 ) in IFA prevents mice from controlling the outgrowth of Ad5E1A-expressing tumors. This indicates that the E1A/IFA vaccine induced suppression rather than induction of E1A-specific CTL immunity. Moreover, administration of the E1A/IFA vaccine to T cell receptor (TCR)-transgenic mice, which express the TCR α and β chains of an E1A-specific CTL clone, strongly suppressed tumor-specific CTL-mediated immunity. These experiments examined the effects of peptide administration on a monoclonal CTL population. To establish whether s.c. E1A-peptide vaccination also induces E1A-specific CTL tolerance at the polyclonal CTL level, wild type (wt) C57BL/6 mice were injected with either E1A-peptide (FIGS. 5a and 5b) or a control peptide FIGS. 5c and 5d). One day later the mice were boosted with a syngeneic cell line expressing high levels of the E1A-peptide at its surface (FIGS. 5b and 5d). Injection of this cell line into mice primed with the control peptide readily induces E1A-specific immunity (FIG. 5d). However, the ability of mice to mount E1A-specific CTL responses was abrogated after injection of the E1A/IFA vaccine (FIG. 5b). These data indicate that injection of the E1A-peptide not only leads to E1A-specific tolerance in TCR-transgenic mice but also in mice expressing a polyclonal E1A-specific T cell repertoire.

Since s.c. injection of the E1A/IFA vaccine leads to systemic CTL tolerance, it was investigated whether the E1A-peptide is dispersed systemically and presented to precursor CTL in the periphery. Therefore, mice were injected s.c. with the E1A-peptide or Human Papilloma Virus (HPV) 16 E7-derived control peptide emulsified in IFA. Spleen cells from these mice were isolated 16h later and used as stimulator cells for an E1A-specific CTL clone in vitro. Splenocytes from mice injected with the E1A-peptide s.c. induced specific proliferation, whereas splenocytes from mice injected with the E7-peptide s.c. failed to do so (FIG. 6). Moreover, a control CTL clone did not proliferate on spleen cells derived from E1A-injected mice (data not shown). Thus, these data indicate that the E1A-peptide injected s.c. in IFA is systemically presented in the periphery by, amongst others, splenocytes.

In view of the tolerizing effects described above of the E1A-peptide vaccine, there was a question whether CD40-triggering in vivo is sufficient to prevent peripheral tolerization of CTL and to restore CTL priming. Therefore, it was investigated whether injection of tolerizing peptides combined with in vivo CD40 triggering could prevent the induction of peripheral CTL tolerance leading to tumor-specific CTL immunity.

In Examples 1 and 2 it has been shown that CD40-triggering in vivo can replace the requirement for CD4$^+$ T helper cells in priming of helper-dependent CTL responses. Since CD4$^+$ T cell-mediated helper activity has been implicated in the prevention of peripheral CTL tolerance induction, the inventors addressed the question whether CD40-triggering in vivo is sufficient to prevent peripheral E1A-specific CTL tolerization. To this end, mice were injected with the E1A/IFA vaccine in combination with the activating anti-CD40 mAb FGK-45. Mice that received this combination mounted strong E1A-specific CTL responses (FIGS. 7b and 7e), whereas mice that received the E1A/IFA vaccine (FIG. 7e) or mAb alone did not (not shown). The combination of E1A/IFA vaccine and anti-CD40 mAb failed to elicit CTL in CD40-deficient mice (FIGS. 7c and 7d). Furthermore, co-injection of the E1A/IFA vaccine with an isotype-matched control mAb (FIG. 6a) or IL-2 failed to convert CTL tolerance induced by the E1A/IFA vaccine into CTL priming (not shown). The range and variation of responses to the E1A-epitope in E1A-peptide only, or E1A-peptide plus anti-CD40-vaccinated animals, is shown in FIG. 7e. Thus, systemic CD40 activation can reverse peptide-induced peripheral CTL tolerance into peptide and tumor-specific CTL mediated immunity.

The induction of E1A-specific immunity strongly correlated with the presence of CD8$^+$ T cells in the spleen of vaccinated mice that stained with PE-conjugated H-2-D$^b$-tetramers containing the E1A-peptide (D$^b$/E1A). Within 10 days after vaccination, CD8$^+$ T cells staining with D$^b$/E1A tetramers could be detected by flow cytometry in mice injected with E1A-peptide and the anti-CD40 mAb, but not in mice injected with E1A-peptide alone (not shown). In the mice injected with E1A-peptide, the percentage of CD8$^+$ cells that stained with the D$^b$/E1A tetramers was approximately 3%. In mice vaccinated with whole adenovirus, which induces potent E1A-specific immunity, comparable amounts of D$^b$/E1A tetramer-reactive CD8$^+$ spleen cells were detected. These results indicate that the expansion of E1A-specific CD8$^+$ T cells in mice that received the E1A/IFA vaccine in combination with the anti-CD40 mAb was substantial and equivalent to that found in virus vaccinated animals.

EXAMPLE 4

CD40-triggering Strongly Enhances the Efficacy of Peptide-based Anti-cancer Vaccines Although the findings described above show that provision of help through CD40-triggering is sufficient to prevent CTL-tolerization after administration of a tolerogenic peptide-vaccine, they do not address the question whether the efficacy of anti-cancer vaccines that normally induce protective immunity, instead of tolerance, can be enhanced by activation through CD40. It was examined whether CD40-triggering in vivo is beneficial to the outcome of vaccination with an HPV16 E7-derived peptide. Vaccination with this peptide induces protective CTL-mediated immunity against a challenge with HPV16-transformed tumor cells. Moreover, this peptide can be used in a therapeutic setting when loaded on in vitro activated DC suggesting that the strength of the anti-tumor response is enhanced when presented by activated DC.

Mice receiving the E7-peptide in combination with CD40-triggering mounted a more potent CTL-response compared to mice treated with E7-peptide only (data not shown), indicating that CD40-triggering also enhances the efficacy of the HPV16 E7-peptide vaccine and confirming the findings with the E1A peptide described above. Moreover, mice treated 6 days after s.c. injection of CD40-negative HPV16 E6/E7 transformed tumor cells with the HPV16 E7-peptide alone (open squares) are able to slow down tumor growth, but eventually most animals succumb to the tumor (FIG. 8). When, however, HPV 16 E7-peptide vaccination was combined with injection of the anti-CD40 mAb, tumor growth was markedly reduced and 7 out of 10 mice rejected the tumor, whereas animals injected with a control peptide and the anti-CD40 mAb were unable to control outgrowth of the tumor. These results show that the effect of vaccination regiments can be markedly enhanced when immunization is combined with in vivo CD40-triggering. These data provide the basis for the development of extremely potent and novel anti-tumor vaccines for cancer patients.

The foregoing description, terms, expressions and examples are exemplary only and not limiting. The invention includes all equivalents of the foregoing embodiments, both known and unknown. The invention is limited only by the claims which follow and not by any statement in any other portion of this document or in any other source.

What is claimed is:

1. A composition comprising an activating anti-CD40 antibody and a CTL-activating peptide.

2. The composition of claim 1 wherein the CTL-activating peptide is a tumor peptide or a viral peptide.

3. The composition of claim 2 wherein the CTL-activating peptide is a tumor peptide.

4. The composition of claim 1 wherein the CTL-activating peptide is selected from the group consisting of:
   (a) a human adenovirus E1A CTL activating peptide that comprises SGPSNTPPEI (SEQ ID NO:2),
   (b) a human adenovirus E1B CTL activating peptide that comprises VNIRNCCYI (SEQ ID NO:1), or
   (c) a human papillomavirus-16 (HPV 16) E7 CTL-activating peptide that comprises RAHYNIVTF (SEQ ID NO: 3).

5. The composition of claim 4 wherein the CTL-activating peptide is said HPV16 E7 CTL-activating peptide that comprises RAHYNIVTF (SEQ ID NO: 3).

6. A pharmaceutical composition comprising the composition of claim 5.

7. The pharmaceutical composition of claim 6 wherein the activating anti-CD40 antibody has reduced immunogenicity to avoid an immune response against itself in a subject to which it is administered.

8. The pharmaceutical composition of claim 7, wherein the activating anti-CD40 antibody is human, humanized, chimeric or Deimmunised™.

9. A method of generating or enhancing a CTL response in an animal, comprising administering to the animal:
   (a) an activating anti-CD40 antibody with reduced immunogenicity to avoid an immune response against itself in the animal; and
   (b) a CTL-activating tumor or viral peptide, in amounts effective to generate or enhance a CTL response specific for the peptide in said animal.

10. The method of claim 9 wherein the CTL-activating peptide is a tumor peptide and said CTL response that is generated or enhanced is specific for said tumor peptide.

11. The method of claim 9 or 10 wherein the animal is a human and the anti-CD40 antibody is human, humanized, chimeric or Deimmunised™.

12. A method of treating a human papillomavirus (HPV)-induced tumor in a subject, comprising administering to the subject the pharmaceutical composition of claim 7.

13. The method of claim 12 wherein the subject is a human and the anti-CD40 antibody is human, humanized, chimeric or Deimmunised™.

14. A method of treating an HPV E7-expressing-tumor in a subject, comprising administering to the subject the pharmaceutical composition of claim 7.

15. The method of claim 14 wherein the subject is a human and the anti-CD40 antibody is human, humanized, chimeric or Deimmunised™.

* * * * *

UNITED STATES PATENT AND TRADEMARK OFFICE
CERTIFICATE OF CORRECTION

PATENT NO. : 7,563,445 B2
APPLICATION NO. : 10/227789
DATED : July 21, 2009
INVENTOR(S) : Cornelius J. M. Melief et al.

Page 1 of 1

It is certified that error appears in the above-identified patent and that said Letters Patent is hereby corrected as shown below:

Item 73, "Keygene N.V., Wageningen, the Netherlands," should read --University Hospital Leiden, Leiden, Netherlands--.

Signed and Sealed this

Tenth Day of November, 2009

David J. Kappos
*Director of the United States Patent and Trademark Office*

SEQUENCE LISTING

```
<160> NUMBER OF SEQ ID NOS: 3

<210> SEQ ID NO 1
<211> LENGTH: 9
<212> TYPE: PRT
<213> ORGANISM: Human adenovirus E1B derived peptide

<400> SEQUENCE: 1

Val Asn Ile Arg Asn Cys Cys Tyr Ile
1               5

<210> SEQ ID NO 2
<211> LENGTH: 10
<212> TYPE: PRT
<213> ORGANISM: Human Adenovirus E1A derived peptide

<400> SEQUENCE: 2

Ser Gly Pro Ser Asn Thr Pro Pro Glu Ile
1               5                   10
```

```
-continued

<210> SEQ ID NO 3
<211> LENGTH: 9
<212> TYPE: PRT
<213> ORGANISM: Human Papilloma Virus Type 16 E7 derived peptide

<400> SEQUENCE: 3

Arg Ala His Tyr Asn Ile Val Thr Phe
1               5
```